United States Patent [19]
Vargas et al.

[11] Patent Number: 5,849,293
[45] Date of Patent: Dec. 15, 1998

[54] USE OF HUMAN TRANSFERRIN IN CONTROLLING INSULIN LEVELS

[75] Inventors: Luis A. Vargas, Santiago, Chile; Carlos H. Faerman; P. Andrew Karplus, both of Ithaca, N.Y.

[73] Assignee: Cornell Research Foundation, Inc., Ithaca, N.Y.

[21] Appl. No.: 585,355

[22] Filed: Jan. 11, 1996

[51] Int. Cl.$^6$ .......................... A61K 39/395; G01N 33/53
[52] U.S. Cl. ..................................... 424/139.1; 424/141.1; 435/7.1; 514/2
[58] Field of Search ................. 514/2; 435/7.1; 424/139.1, 141.1

[56] References Cited

U.S. PATENT DOCUMENTS

| | | | |
|---|---|---|---|
| 4,505,897 | 3/1985 | Coy et al. | 514/11 |
| 4,871,835 | 10/1989 | Aviv et al. | 530/399 |
| 5,281,581 | 1/1994 | Cooper et al. | 514/12 |
| 5,350,836 | 9/1994 | Kopchick et al. | 530/399 |
| 5,371,189 | 12/1994 | Helderman | 530/350 |
| 5,405,750 | 4/1995 | Suciu-Foca et al. | 435/724 |

FOREIGN PATENT DOCUMENTS

| | | |
|---|---|---|
| 324969-A2 | 12/1988 | European Pat. Off. |
| 443790-A1 | 2/1991 | European Pat. Off. |
| WO 93/10819 | 6/1993 | European Pat. Off. |
| WO 95/00852 | 1/1995 | European Pat. Off. |

OTHER PUBLICATIONS

Ishibashi, F., "Glomerular Clearance and Tubular Reabsorption of Transferrin Microtransferrinuric Patients with Non--insulin-Dependent Diabetes," *Diabetes Research and Clinical Practice*, 25(3):169–75 (1994).

Fagerberg, et al., "Carbohydrate-Deficient Transferrin is Associated with Insulin Sensitivity in Hypertensive Men," *J. Clin. Endocrin. & Metab.*, 79(3):712–15 (1994).

Schaefer, et al., "A New Transgenic Mouse Model of Chronic Hyperglycemia," *Diabetes*, 43:143–53 (1994).

Akin et al., Cancer Letters, 69, 51–57 (1993).

Dittman et al., Biochemical & Biophysical Research Communications, 176, 473–478, 1991.

*Primary Examiner*—Stephen Walsh
*Assistant Examiner*—Nirmal S. Basi
*Attorney, Agent, or Firm*—Nixon, Hargrave, Devans & Doyle LLP

[57] ABSTRACT

The present invention relates to the use of transferrin in controlling insulin levels. Transferrin can disrupt insulin:receptor interactions in mammalian cells, may be used in mammals to treat hypoglycemia, may also be used to inhibit production of insulin by mammalian cells, and can decrease the serum insulin levels in a mammal. The invention further provides methods for identifying compounds which modulate the effect of transferrin on insulin signal transduction. Pharmaceutical compositions containing transferrin are also disclosed.

6 Claims, 6 Drawing Sheets

USE OF HUMAN TRANSFERRIN IN CONTROLLING INSULIN LEVELS

The subject matter of this application was made with support from the United States Government under Grant No. 1P01GM48874 from the National Institutes of Health. The U.S. Government may retain certain rights.

FIELD OF THE INVENTION

The present invention relates to the use of human transferrin in controlling insulin levels.

BACKGROUND OF THE INVENTION

Diabetes mellitus is the most common of the serious metabolic diseases affecting humans. It has been estimated that there are over 200 million diabetics in the world. (See J. Steinke and J. S. Soeldner, *Diabetes Mellitus in Principles of Internal Medicine*, 8th ed., 563 (1977) Diabetics not only face a decreased life expectancy but also the ever-present possibility of disabling complications.

Metabolically, diabetes is characterized by an inappropriate elevation of blood glucose levels. In type I Diabetes Mellitus, this is due to an absence of insulin in the individual. In type II Diabetes Mellitus, although there is circulating insulin, its signal is not efficiently transduced via the insulin receptor, giving rise to insulin resistance, where the body responds less and less well to a given amount of insulin. Insulin is a peptide hormone which is produced by the Langerhans islets in the pancreas. Insulin triggers increased glucose utilization, protein synthesis, and the formation and storage of neutral lipids. The present invention focuses on Type II diabetes mellitus or non-insulin-dependent diabetes.

Diabetes mellitus is also characterized by long term complications involving the eyes, nerves, kidneys, and blood vessels. These diabetic complications include premature atherosclerosis, intercapillary glomerulosclerosis, retinopathy, and neuropathy. The major cause of morbidity and mortality among diabetics is coronary heart disease. M. J. Garcia, McNamara, P. M., Gordon, T., Kannell W. E., *Diabetes* 34:105–111 (1974).

The increased blood glucose levels are associated with altered lipid and protein metabolism. Increased serum glucose concentrations leads to an increase in non-enzymatic glycation of various proteins, such as hemoglobin in erythrocytes and albumin in the serum. Non-enzymatic glycation of proteins can affect the normal activity in the body. For instance, Cu, Zn-superoxide dismutase, which traps superoxide radicals, is inactivated by glycation reaction. Glycation-induced changes in the activities of body proteins has been postulated to be a contributor to the pathology of diabetes. Brownlee, "Glycosylation Products as Toxic Mediators of Diabetic Complications" *Annu. Rev. Med.* 42:159–66 (1991).

The primary goal in treatment of all types of diabetes is to maintain blood glucose levels as close to normal as possible. For type II diabetes, the first line of therapy for maintaining blood glucose levels is modification of diet and lifestyle. The diabetic diet features restrictions on fat content and an increased intake of dietary fiber. Regular exercise is also emphasized to decrease weight and reduce the degree of insulin resistance.

If diet and lifestyle modifications fail to control glucose levels, a trial of either oral hypoglycemic therapy or insulin therapy is required to control glucose levels and thus minimize complications related to the disease.

Type II diabetics who cannot control their blood glucose levels through diet and exercise may respond to sulfonylurea drugs (e.g. glibenclamide). See Bailey, C. J., "The Problem of Insulin Resistance", *The Genetic Engineer and Biotechnologist*, Biopaper No. 12.5.53 (1992). These drugs act primarily by increasing the level of insulin production from the remaining active pancreatic beta cells. However, these compounds may have serious complications. For example, sulfonylureas may lead to dangerous hypoglycemic reactions including coma. Furthermore, these compounds may not be used in diabetic patients with hepatic or renal insufficiency. Sulfonylureas also produce gastrointestinal side effects which are not well tolerated by many of the patients. See Jackson, R. A., et al., *Diabetes*, 36:632–40 (1987). As the disease progresses, the conditions of a substantial number of patients worsen to the point where oral agents cannot adequately control blood glucose levels and insulin therapy becomes necessary. Gray, H., and O'Rahilly, S., *Archives of Internal Medicine*, 155: 1137 (1995). Other compounds used to treat diabetes such as, biguanide and metformin also have serious drawbacks.

Although advances in treating diabetes havegreatly extended the lives of diabetics, they still cannot expect a normal life expectancy. Furthermore, diabetics must suffer the long term degradative effects of diabetes, including blindness, renal insufficiency, heart disease, and gangrene of the feet. New methods are needed to increase glycemic control, in order to lessen the adverse effects of diabetes.

Since the pioneering work by Houssay (B. A. Houssay, A. Biasotti, E. Di Benedetto, and C. T. Rietti, *Compt. R. Soc. Biol. Paris* 112:494 (1932)), many studies have documented a strong connection between growth hormone ("GH") and glycemia, with hypoglycemia acting to increase GH levels (J. Roth, S. H Glick, R. S. Yallow, and S. A. Berson, *Science* 140:987 (1963)) and GH acting to cause insulin resistance (N. Venkatesan, et al., "Insulin Resistance in Rats Harboring Growth Hormone-secreting Tumors: Decreased Receptor Number but Increased Kinase Activity in Liver," *Metab. Clin. Exp.* 44:75–84 (1995)) and hyperglycemia (M. Press, et al., "Effect of Insulin on Growth Hormone-Induced Metabolic Derangement in Diabetes," *Metab. Clin. Exp.* 35:956–59 (1986). As reviewed by Sönksen et al (P. H. Sönksen, D. Russell-Jones, and R. H. Jones, *Horm. Res.* 40:68 (1993)), high levels of GH are diabetogenic, and the lowering of GH by hypophysectomy often improves the control of diabetes mellitus, and can halt the progression of retinopathy. Unfortunately, the physiological rationale for these effects of GH, and the molecular mechanism by which GH modulates blood glucose levels have not been elucidated.

U.S. Pat. No. 5,350,836 to Kopichick et al. discloses treating diabetes patients with antagonists of growth hormone. Similarly, U.S. Pat. No. 4,505,897 to Coy, et al., identified a relationship between somatostatin antagonists and increased levels of growth hormone and insulin. However, growth hormone is not able to antagonize successfully the action of insulin in the first 120 minutes. P. De Feo et al., *Am. J. Phys.* 256:E835 (1989), B. R. Pal, P. E. Phillips, D. R. Mathews, and D. B. Dunger, *Diabetologia* 35:542 (1992).

The possibility that GH effects are mediated by a natural insulin antagonist found in the human plasma (L. Vargas, et al., *Biochem. J.* 77:43 (1960); K. W. Taylor, L. Vargas, and P. J. Randle, *Lancet* 1:1313 (1960)), which is induced by administration of GH (L. Vargas, M. Bronfman, and M. E. Kawada, *Horm Metab. Res.* 6:275 (1974)), have been pursued for many years. Insulin antagonism induced by growth hormone was believed to be associated with a glycoprotein (L. Vargas, et al., *Excerpta Med. Internat. Congress. Series* 209, Abstract 82 (1970)) found in the α2-globulin fraction of normal plasma. This fraction has been referred to as the α2-inhibitor or α2-glycoprotein (α2-GP). α2-GP appears to be produced by the liver about 2 hours after exogenous treatment with GH, or after endogenous stimulation of GH by stress and chlorpromazine, or by insulin-induced hypoglycemia. L. Vargas and M. E. Kawada, *Horm Metab. Res.* 8:383 (1976); L. Vargas and M. E. Kawada, *Horm. Metab. Res.* 17:259 (1985); L. Vargas, et al., *Arch. Biol. Med. Exper.* 6:54 (1969). Clinical observations demonstrate that both the production and action of α2-GP are independent of the adrenal gland. L. Vargas and M. E. Kawada, *Horm Metab. Res.* 8:383 (1976). In hypophysectomized patients or patients with panhypopituitarism, plasma insulin activity is normal whereas α2-GP activity is not detectable by in vitro assays, but it reappears after GH administration. K. W. Taylor, L. Vargas, and P. J. Randle, *Lancet* 1:1313 (1960). On the other hand, in one patient with an excess of GH (acromegaly), high levels of α2-GP activity are present, and, after hypophysectomy, the activity of α2-GP disappears and insulin reappears. K. W. Taylor, L. Vargas, and P. J. Randle, *Lancet* 1:1313 (1960).

Although, α2-GP has been identified as an insulin antagonist, its identity and characteristics have not been determined. The present invention is directed to advancing beyond this state of the art.

SUMMARY OF THE INVENTION

The present invention relates to transferrin's activity as an insulin antagonist. The present invention provides a method for disrupting the interaction between insulin and the insulin receptor in mammalian cells by administering an effective amount of transferrin to the mammalian cells.

Another embodiment of the present invention is directed to a pharmaceutical composition containing transferrin and a pharmacologically-acceptable carrier.

Another aspect of the invention is a method of treating hypoglycemia by administering an effective amount of transferrin to a mammal suffering from or susceptible to hypoglycemia.

The invention also embodies a method for modulating the effects upon insulin signal transduction in mammalian cells. This is accomplished by administering to mammalian cells a compound which inhibits transferrin expression or inhibits transferrin interaction with either insulin or insulin receptors.

A further aspect of the invention is a method of decreasing insulin production by mammalian cells by administering an effective amount of transferrin to the mammalian cells. Similarly, the serum concentration of insulin in mammals can be decreased through administration of an effective amount of transferrin to the mammal.

A further embodiment of the present invention is a method of identifying compounds for the treatment of diabetes. First, a mixture of insulin, insulin receptor, transferrin, and a test material is formed. It is then determined whether the mixture with the test material produces a level of insulin:receptor complex greater than the level of insulin:receptor complex in a mixture where the test material is absent.

Another aspect of the invention is a method of identifying compounds for the treatment of diabetes in mammalian cells. The mammalian cells are treated with a mixture of insulin, transferrin, and a test material. It is then determined whether the cell in the presence of the test material achieves greater expression of an insulin responsive gene than cells treated with the mixture where the test material is absent.

DETAILED DESCRIPTION OF THE INVENTION

Figure 1:
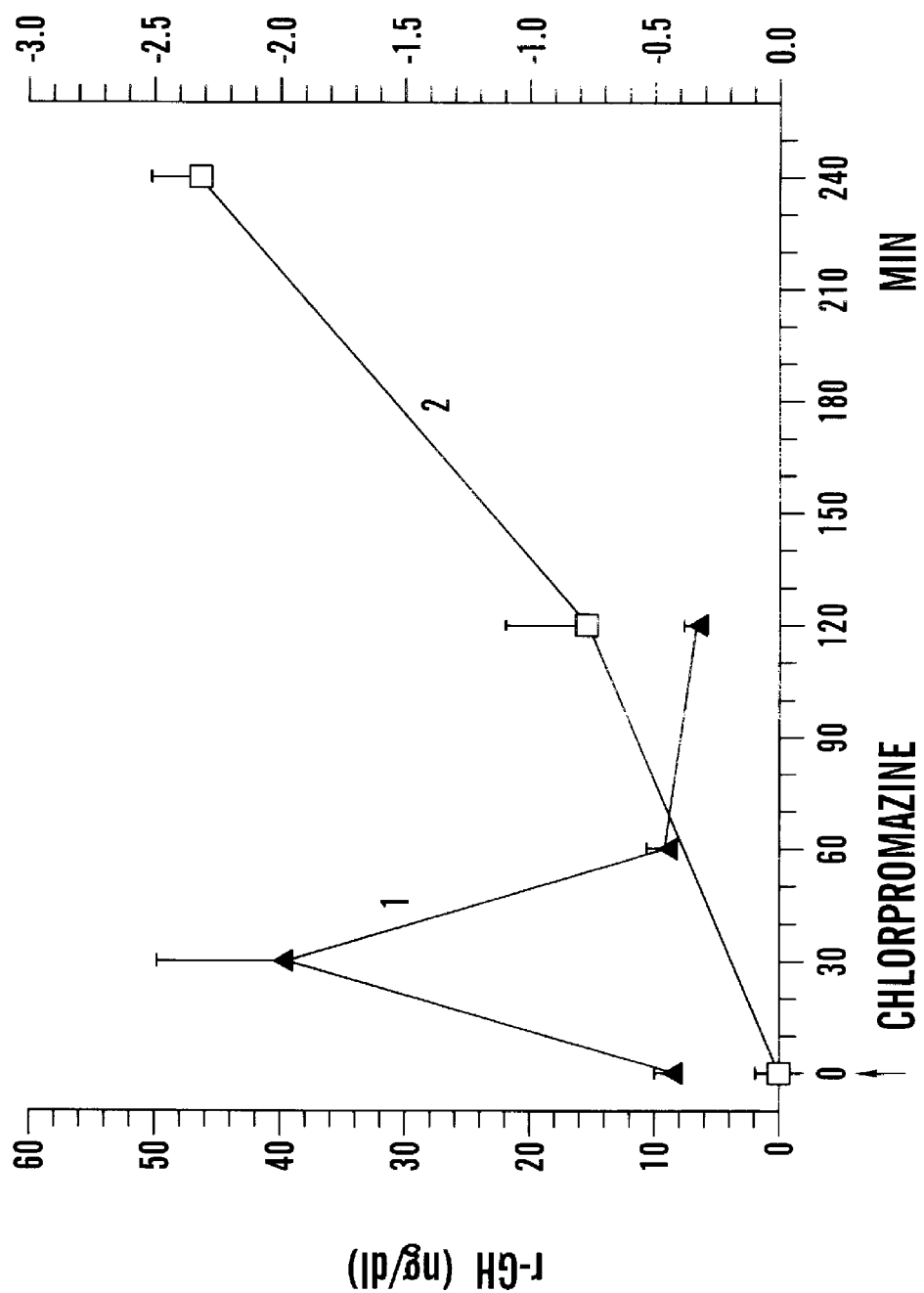
FIG. 1 shows the time-course of α2-GP induction by endogenous GH.

The present invention relates to transferrin's activity as an insulin antagonist. The present invention provides a method for disrupting the interaction between insulin and the insulin receptor in mammalian cells by administering an effective amount of transferrin to the organism.

α2-GP was purified from the plasma of normal individuals by ammonium sulfate precipitation followed by affinity chromatography on concanavalin A-sepharose and gel filtration on Sephadex G-100 to yield a single 80-kD band by SDS-gel electrophoresis. The time-course of α2-GP induction shows that pure α2-GP reproduces the key insulin antagonistic and diabetogenic effects of GH in vivo. Furthermore, α2-GP is identical to the well-studied iron carrier protein human serum transferrin ("hsTf").

Transferrin is fully discussed in Welch, S., *Transferrin: The Iron Carrier*, CRC Press, Boca Raton (1992) and the references cited therein, which are hereby incorporated by reference. Transferrin is a glycoprotein which is needed for the transportation of iron in the blood of more complex organisms. In humans, transferrin is a plasma glycoprotein with a molecular weight of approximately 80,000 daltons and is able to bind reversibly to two atoms of ferric iron in the presence of bicarbonate. Related proteins have been found in all mammals, birds, reptiles, amphibians, bony fish, and cartilaginous fish.

The body of an adult contains about 14 grams of transferrin, half of which is found in the blood plasma. The remainder of the transferrin is found in other body fluids including lymph, tears, cerebrospinal fluid, bile, amniotic fluid, milk, saliva, aqueous humor, aqueous vitreous, and seminal fluid. Plasma transferrin, at a concentration of 2.5 grams per liter accounts for 4% of all the protein in blood.

Sufficient quantities of the protein were available for determination of the protein sequence. The complete sequence of 679 amino acids was determined by protein sequencing methods and later verified by the cloning and sequencing of the gene. The most remarkable feature of the protein sequence is the high degree of homology between the N- and C-terminal halves of the protein. There are 336 amino acids in the N-terminal portion of the protein which have a 42% identity with the counterparts in the C-terminal domain. It has been postulated that the structure is a result of a gene duplication.

Amino acid sequences of additional members of the human siderophilin family, such as lactoferrin and melanotransferrin, have a similar degree of homology between the C- and N-terminal domains. See Met-Boutique, M., et al., "Human Lactoferrin: Amino Acid Sequence and Structural Comparison With Other Transferrins," *Eur. J. Biochem.*, 145:659 (1984); Rose, T. M., et al., "Primary Structure of Human Melanoma-Associated Antigen p97 (Melanotransferrin) deduced from the mRNA sequence," *Proc. Nat. Acad. Sci. USA* 83:1261 (1986); which are hereby incorporated by reference. This suggests that the proteins must have arisen from a common ancestor. See MacGillivray, R. T. A., et al., "The Primary Structure of Human Serum Transferrin," *J. Biol. Chem.* 258: 3543 (1983), which is hereby incorporated by reference.

The tertiary structure of transferrin has been elucidated. Bailey, S., et al., "Molecular Structure of Serum Transferrin at 3.3 Angstrom Resolution," *Biochemistry*, 27:5804 (1988), which is hereby incorporated by reference. The polypeptide chain is folded into two globular lobes joined by a short intervening region. The N-lobe, comprising the N-terminal half of the protein, contains the first 330 amino acid residues. The C-lobe, comprising the C-terminal half of the protein, contains the last 330 amino acids. Each lobe is an ellipsoid and contains one iron binding site. The two lobes are connected by a short three turn helix of 15–20 amino acids.

The N and C-lobes of transferrin have similar tertiary structure as expected from their amino acid sequence similarity. The N and C-lobes each contain a deep cleft which divides the lobe into two dissimilar regions, Domains I and II. The cleft between these domains contains the amino acid residues which form the iron binding site.

Human transferrin is a glycoprotein with two N-linked oligosaccharide chains attached to asparagine residues 413 and 611 in both the C-lobe. The structure of these sugar chains can vary greatly. This phenomenon is referred to as microheterogeneity. Microheterogeneity is a result of the mechanism of protein glyosylation in eukaryotes. Glycoprotein glycan chains are synthesized in a sequential process of enzyme-catalyzed addition and removal of sugar residues as the protein passes through the endoplasmic reticulum. See Roth, J., "Subcellular Organization of Glycosylation in Mammalian Cells," *Biochem. Biophys. Acta* 906:405 (1987), which is hereby incorporated by reference. The compartmentalization of the enzymes and their substrates in the endoplasmic reticulum can profoundly affect the glycan structure of the glycoprotein. Furthermore, transferrin is bound and taken back up by the cell during the intracellular iron cycle, the glycan chains are subject to degradation and modification.

Transferrin invariably carries two types of complex glycan chains. Much of the microheterogeneity of the glycan chains is due to differences in the degree of branching and the nature of the sugar residues at the outermost ends of the branches. As many as nine different isoforms of transferrin, resulting from variable sialic acid content, have been identified in human serum. In addition, the proportion of the nine different isoforms is known to be significantly altered in a number of conditions including insulin sensitivity, pregnancy, and alcoholism. See Fagerberger, B., et al., *J. of Clin. Endocrin. Metabol.*, 79:712 (1994), which is hereby incorporated by reference.

Transferrin migrates electrophoretically with the β-globin fraction of human serum and is easy to identify with nonspecific stains such as Coomassie Blue because of its high concentration. The presence of transferrin can be verified by using a more specific technique such as an iron stain like Nitroso R or by immunofixation. See Meuller, J. O., et al., "Transferrin Variation in Columbidae," *Genetics* 47:1385 (1962), which is hereby incorporated by reference.

In non-denaturing conditions, the isoelectric point of transferrin is affected by iron saturation. Under normal physiological conditions, serum transferrin is about 30% saturated. Therefore, transferrin exists in four different forms with respect to iron content in serum: apo-transferrin, having no iron; monoferric transferrin with an iron atom attached to the N-terminal domain binding site; monoferric transferrin with an iron atom attached to the C-terminal domain binding site; and diferric transferrin with one iron bound to N- and one bound to C-. The binding of iron to transferrin results in the release of three protons. Further, the protein undergoes a conformational change upon iron binding resulting in a more spherical shape and an alteration of the positions of the N-glycan chains relative to the protein. As a result, at alkaline pH, diferric transferrin has a lower pI (5.5) than apotransferrin (pI 5.9). At normal electrophoresis conditions, i.e. pH 8.9, these charge differences are not apparent.

The gene encoding transferrin has been carefully studied. In 1984, the isolation and structureof a portion of the human transferrin cDNA was reported. The cloned fragment was approximately 1000 base pairs in length and it encoded for the C-terminal portion of the protein. A complete sequence of the gene, a 2324-bp cDNA, was published three months later. Yang, et al., *Proc. Nat. Acad. Sci. USA,* 81:2752 (1984), which is hereby incorporated by reference. The gene sequence indicated the presence of an additional 19 amino acids at the N-terminal of the protein. It has been determined that these 19 amino acids are a signal peptide which are cleaved from the protein during secretion.

The sequence of the human transferrin gene has also been deduced. The sequence includes 33,500 base pairs. It is organized into 17 coding exons which are separated by 16 introns which range in size from 675 to 5300 bp.

In a further embodiment of this method, either insulin or growth hormone is administered to a mammal together with transferrin. Insulin administration results in a rapid decrease in blood sugar levels, and, as the insulin is cleared from the mammal, the blood sugar level may increase. The administration of exogenous serum transferrin with exogeneous insulin can produce better glycemic control. Similarly, serum transferrin may be administered simultaneously with growth hormone. Growth hormone antagonizes insulin but only after a two hour delay. The combination of serum transferrin and growth hormone administration can extend the insulin antagonism effect over an extended period.

Other embodiments of the invention include methods for administering the transferrin to mammalian cells. The transferrin may be administered as a pharmaceutical composition containing transferrin with a pharmacologically-acceptable carrier and, optionally, insulin or growth hormone.

The present invention may be carried out by binding transferrin to insulin or to the insulin receptor or by disrupting intracellular signal transduction from the insulin receptor to mammalian cells.

Another aspect of the invention is a method of treating hypoglycemia by administering an effective amount of transferrin to a mammal suffering from or susceptible to hypoglycemia.

The invention also embodies a method for modulating the effects upon insulin signal transduction in mammalian cells. This is accomplished by administering to mammalian cells a compound which inhibits transferrin expression or inhibits transferrin interaction with either insulin or insulin receptors.

A preferred embodiment of this method is where the compound inhibits the expression of transferrin. As an example, the level of transferrin protein expression in the presence of test compounds may be determined by using recombinant cells carrying a reporter molecule linked to the serum transferrin gene. The cells are exposed to test materials and the level of expression of the transferrin gene is measured. Methods for this procedure are well known to those skilled in the art. See Maniatis, et al., *Molecular Cloning: A Laboratory Manual*, Cold Springs Laboratory, Cold Springs Harbor, N.Y. (1982), which is hereby incorporated by reference. Alternatively, expression of transferrin may be measured spectrophotometrically due to its iron binding capability. When transferrin binds free iron, it exhibits a reddish color.

Compounds which inhibit transcription of the transferrin gene are identifiable by determining the level of transcription in the presence of the test material. Transcription can be measured though the use of a reporter molecule as above or through the use of probes which can hybridize to the mRNA. The procedures for hybridization assays are well known to those skilled in the art.

Another preferred embodiment of this method is where the compound inhibits the interaction with either insulin or insulin receptors.

A more preferred aspect of this method is where the compound is an antibody which can bind to transferrin. Even more preferred is where the antibody is a monoclonal antibody.

Another more preferred embodiment of the invention is where the compound is a soluble transferrin receptor. An equally preferred embodiment is a fragment of a transferrin receptor capable of binding transferrin.

Procedures for raising polyclonal antibodies are well known. Typically, such antibodies can be raised by administering one of the proteins or polypeptides of the present invention subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in E. Harlow, et. al., editors, *Antibodies: A Laboratory Manual* (1988), which is hereby incorporated by reference.

Monoclonal antibody production can be carried out using BALB/c mice. Immunization of the B-cell donor mice can involve immunizing them with antigens mixed in Titer-Max™ adjuvant as follows: 50 $\mu$g antigen/20 $\mu$l emulsion×2 injections given by an intramuscular injection in each hind flank on day 1. Blood samples can be drawn by tail bleeds on days 28 and 56 to check the titers by ELISA assay. At peak titer (usually day 56) the mice can be subjected to euthanasia by $CO_2$ inhalation, after which splenectomies can be performed and spleen cells harvested for the preparation of hybridomas by standard methods.

In addition to utilizing whole antibodies, the processes of the present invention encompass use of binding portions of such antibodies. Such antibody fragments can be made by conventional procedures, such as proteolytic fragmentation procedures, as described in J. Goding, *Monoclonal Antibodies: Principles and Practice*, pp. 98–118 (N.Y. Academic press 1983), which is hereby incorporated by reference. Similar methods may be used to generate serum transferrin fragments or mutants for use in the invention.

Another aspect of the invention is where the administering of compounds, to modulate the effects of transferrin upon insulin signal transduction, involves administering the compound to a mammal to effect diabetic control.

A further aspect of the invention is a method of decreasing insulin production by mammalian cells by means of administering an effective amount of transferrin to the mammalian cells.

Another embodiment of the invention is a method of decreasing the serum concentration of insulin in a mammal through the administration of an effective amount of transferrin to the mammal.

This invention is directed to the treatment of diabetes.

Certain aspects of invention are directed to use in mammals. A preferred embodiment of this invention is where the mammal is a human. Other embodiments of this invention are directed to use in mammalian cells. A preferred embodiment of this invention is where the mammalian cells are human cells.

The agents of this invention can be administered to mammals orally, interparenterally, subcutaneously, intravenously, intramuscularly, intraperitoneally, by intranasal instillation, by application to mucous membranes, such as, that of the nose, throat, and bronchial tubes, or by instillation into hollow organ walls. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the proteins or polypeptides of the present invention or the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The proteins or polypeptides of the present invention or the antibodies or binding portions thereof of this invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the proteins or polypeptides of the present invention or the antibodies or binding portions thereof of the present invention, in solution or suspension, may be packaged in a pressurized aerosol container together with suitable propellants. For example, hydrocarbon propellants like propane, butane, or isobutane with conventional adjuvants can be utilized. The materials of the present invention also may be administered in a non-pressurized form such as in a nebulizer or atomizer.

The agents of the present invention may be administered to cultured cells as a pure solid form, a salt, a suspension or dissolved in a suitable solvent. Examples of suitable solvents include water, alcohols, and dimethyl-sulfoxide.

The present invention involves the use of transferrin preferably human transferrin.

A further embodiment of the present invention is a method of identifying compounds for the treatment of diabetes. First, a mixture of insulin, insulin receptor, transferrin, and a test material is formed. Then, it is determined whether the mixture with the test material produces a level of insulin:receptor complex greater than the level insulin:receptor complex in a mixture where the test material is absent.

For the purposes of this invention, the order of addition in the formation of the mixture may be varied. The transferrin may be added to the mixture prior to the addition of insulin. The transferrin may then bind to the insulin receptor prior to addition of the insulin. Alternatively, transferrin may be added after both insulin and the receptor are in the mixture. The insulin:insulin receptor complex would then be measured at a steady state level.

The preferred method of determining whether the test material produces a greater level of insulin:receptor complex involves separating the insulin:receptor complex from the mixture using antibodies. The antibodies which are specific to insulin, insulin receptor, or the complex are linked to a marker. The antibodies to either of the proteins are used to precipitate the complex. The complex formed could then be quantitated by measuring the amount of the protein which was precipitated. An equally preferred method of determining whether the test material produces a greater level of insulin:receptor complex involves separating the insulin:receptor complex from the mixture by electrophoresis under non-denaturing conditions.

Another aspect of the invention is a method of identifying compounds for the treatment of diabetes in mammalian cells. The mammalian cells are treated with a mixture of insulin, transferrin, and a test material. It is then determined whether the cell in the presence of the mixture produces greater expression of an insulin responsive gene than cells treated with the mixture where the test material is absent.

For the preferred embodiments of this invention, transferrin, insulin, insulin receptor are human transferrin, human insulin, and human insulin receptor, respectively.

EXAMPLES

Experiments were performed on non-fasted male Sprague-Dawley rats from the Faculty of Biological Sciences (Pontifical Catholic University of Chile) and maintained at 21° C. under a 12 h light cycle. The rats remained in the laboratory for 1 h before starting the experiments to avoid novelty stress, necessary to obtain a basal glycemic level of 90 mg/dl. Administration of substances was by intraperitoneal route with the injection volume adjusted to saline 0.5 ml/100 g. The doses were per 100 g body weight, usually for a 200 g rat. Glycemia determination of blood samples collected from the rat tail tip, glycosuria, adrenal medullectomy and 80% pancreatectomy were carried out as previously described. Vargas, L., and M. E. Kawanda, *Horm. Metab. Res.* 6:275 (1974) and Sanchez, R., L. Vargas, *Brain Research* 452:149 (1988), which are hereby incorporated by reference. Surgical operations were performed under general ether anesthesia. Reagents were from Sigma and Ames, USA, Elkhart, Ind., from Hoechst, Frankfurt, Germany and rapid insulin from Novo Nordisk AS, Bagsvaerd, Denmark. Insulinemia was determined in the serum of rats killed under general ether anaesthesia, after 0, 30, 60, 90 and 120 min (3 rats per point), A. Foradori et al., *Rev. Med. Chile* 106:626 (1978), which is hereby incorporated by reference. Rat-GH was measured by Dr. Arnaldo Foradori (Pontifical Catholic University of Chile) following the protocol provided by Dr. A. P. Parlow (Pituitary Hormone Center, Torrence Calif., USA) who also supplied rat-GH.

Example 1

Purification of $\alpha$2-GP

Figure 6A:
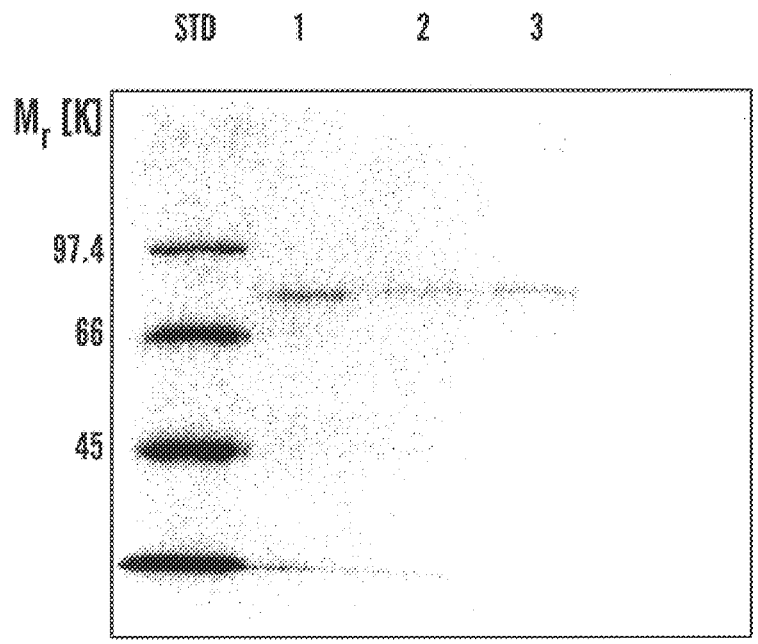
FIG. 6A shows an SDS-PAGE gel (7.5%) comparing α2-GP and hsTf (Sigma), lane 1 (α2-GP), lane 2 (hsTf).

Ammonium sulfate was added to serum isolated from normal individuals to 50% saturation over 30 min at 0° C. After centrifugation at 10,000 rpm for 20 min, the 2.0–2.8M precipitate was dissolved in distilled water, dialyzed extensively at 4° C., and lyophilized. A fraction of this precipitate, 1 g, was then dissolved in 10 ml of 20 mM Tris-HCl pH 7.4 buffer with 0.2M NaCl and applied to a 1.5×27 cm concanavalin A-sepharose column (purchased from Sigma Chemical Co., St. Louis, Mo.) equilibrated with this buffer at room temperature. After washing the column with the same buffer until absorbance (280 nm) dropped to basal values, 50 mM $\alpha$-methyl D-manno-pyranoside was added to release $\alpha$2-GP from the column. This fraction was applied to a Sephadex G-100 1.6×90 cm column (Sigma Chemical Co., St. Louis, Mo.) equilibrated with 0.05 m Tris-HCl 0.1M KCl, pH 7.4. The fractions containing $\alpha$2-GP were pooled, dialyzed, and lyophilized. The isolated protein yielded a single 80-kD band on SDS-gel electrophoresis. See FIG. 6.

Example 2

Time-Course of $\alpha$2-GP Induction

Intact rats were treated with 6.5 mg of chlorpromazine, a drug which causes the hypothalamus to release GH-releasing factor which in turn stimulates GH release. The hypothalamic action of chlorpromazine was demonstrated by Y. Kato, et al., *J. Endocrinol.* 62, 688 (1974), which is hereby incorporated by reference, using somatostatin, a hypothalamic hormone which specifically inhibits GH secretion. GH levels were measured at 10, 30, 60, and 120 min. The GH pulse peaked after 30 min. at about 40 ng/ml above basal levels (CURVE 1 (FIG. 1), r<0.001). A high dose was selected to provoke a large GH pulse which would facilitate early measurements of the induced $\alpha$2-GP. $\alpha$2-GP levels were measured using the standard assay for the inhibition of glucose uptake by rat diaphragm cells in vitro in mg of glucose/g of diaphragm×hour. Vargas, L., et al., *Biochem. J.* 77:43 (1960) and L. Vargas and M. E. Kawada, Horm Metab. Res. 8:383 (1976), which are hereby incorporated by reference. The α2-GP first appears at 120 min (curve 2, p<0.05) and is greater at 240 min (p<0.001). In other experiments where intact rats were subjected to 60 min. of cold and restrained stress (L. Vargas and M. E. Kawada, *Horm Metab. Res.* 8:383 (1976), which is hereby incorporated by reference), it is known that α2-GP increases significantly 60 min. post-stress. Results are mean ± s.e.m., n=3 where n is the number of rats used in these experiments.

Example 3

Effects of Pure α2-GP on Blood Glucose Levels

Figure 2:
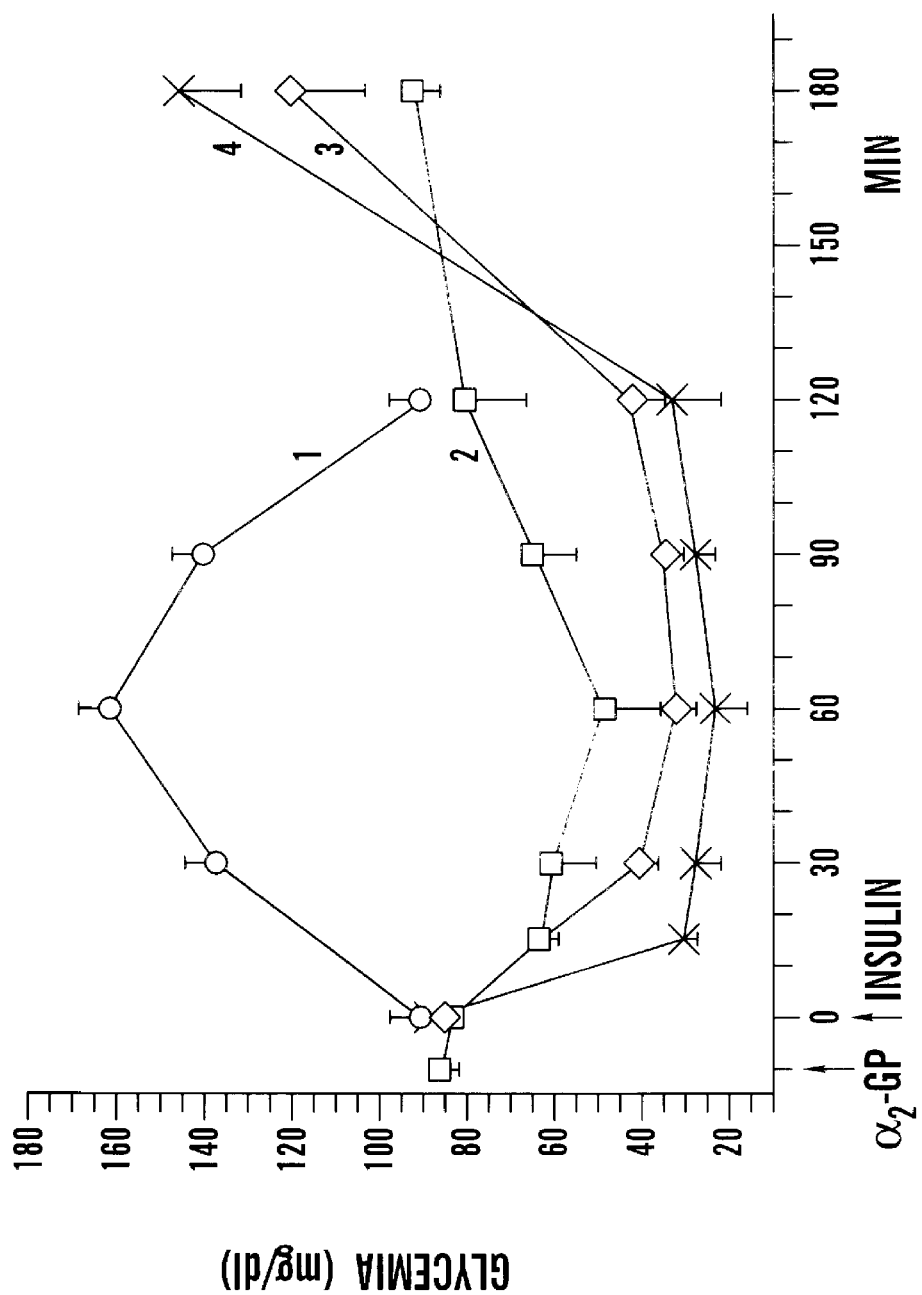
FIG. 2 shows the inhibition of severe insulin-induced hypoglycemia by α2-GP in intact rats.

To document the effects of pure α2-GP on blood glucose levels, intact rats were treated with α2-GP alone or in association with a high, hypoglycemia-inducing dose of insulin. Inhibition of severe insulin-induced hypoglycemia by α2-GP occurred in five intact rats (n=5). In all cases, 0.4 I.U. insulin per 100 g body weight was used to induce hypoglycemia. This is a high dose of insulin since 0.3 I.U. of insulin produce a 50% decrease in the glycemia levels. L. Vargas and M. E. Kawada, *Horm. Metab. Res.* 8:259 (1985) and L. Vargas, et al., *Arch. Biol. Med. Exper.* 6:54 (1969), which are hereby incorporated by reference. As shown in FIG. 2, the effects of 200 μg α2-GP injected alone (curve 1), 10 min before insulin (curve 2, p<0.001 at 120 min), 10 min after insulin (curve 3), and insulin control (curve 4) were studied. Consistent with the high dose of insulin used, the insulin control developed severe hypoglycemia with one of the rats dying at 120 min with no detectable blood glucose. α2-GP alone leads to a rapid and broad hyperglycemia, and, when given 10 min before insulin, it shows a remarkable ability to antagonize the insulin-induced hypoglycemia.

The antagonism was such that the attenuated hypoglycemia was normalized at 120 min and the hyperglycemic rebound seen in the control at 180 min was avoided. Since a significant induced appearance of α2-GP takes 120 min, such delay would be a handicap to achieve an effective anti-insulin blood level of α2-GP. Therefore, to administer previously α2-GP would help the glycemic recovery, as it occurs (FIG. 2, curve 2)). This behavior is quite different from GH and epinephrine, neither of which are able to antagonize effectively the action of insulin within the first 120 minutes. Thecontrols carried out with GH and epinephrine match the known properties of these compounds on blood glucose regulation. When given alone, GH initially lowers blood glucose levels and causes hyperglycemia only after a 120 to 180 min lag time. P. De Feo et al., *Am. J. Phys.* 256:E835 (1989) and B. R. Pal, et al., *Diabetologia* 35:542 (1992), which are hereby incorporated by reference. When given 10 min after insulin treatment, α2-GP was not able to ameliorate the hypoglycemia. In 80%-pancreatectomized (80%-P) rats, a hypersensitive model system for studying the diabetogenic effects of GH. B. A. Houssay, A. Biasotti, and C. T. Rieti, *Comp. R. Soc. Biol. Paris* 111:479, (1932), which is hereby incorporated by reference. The partially pancreatectomized animal, like 80%-P rat, is hypersensitive to insulin. It was devised by Houssay and employed to show the diabetogenic effect of GH. 80%-P rats were used for a sensitive "hyperglycemic test". The response is positive whenever the glycemia increase is statistically significant. Increasing levels of α2-GP gave a typical dose-response curve with the highest levels of α2-GP producing transient diabetes. Significant transient diabetes (hyperglycemia>80 mg/dl over basal levels and >1% glycosuria) was reached at 90 min with 500 μg α2-GP and lasted ~4 h. With 1000 μg of α2-GP, hyperglycemia reached 140 mg/dl over the basal level, and the transient diabetic effect lasted ~8 h.

Example 4

Effect of α2-GP on Insulin Levels

Figure 3:
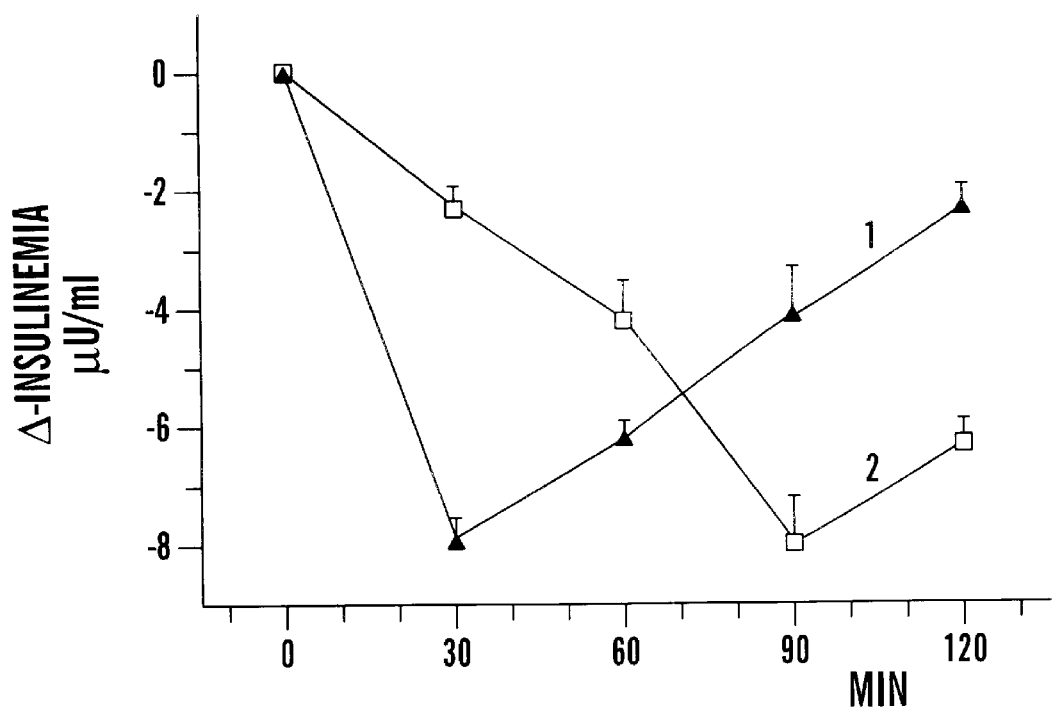
FIG. 3 shows insulin levels in 80%-P rats after treatment with 50 μg α2-GP (curve 1) or after 60 min of restrained-stress (curve 2). The ordinate reports the change in insulin levels (Δ-insulinemia).

Further use of the 80%-P rat model to assess the effect of α2-GP on insulin levels showed that α2-GP causes a rapid and profound hypoinsulinemia (FIG. 3, curve 1). Insulin levels were monitored in 80%-P rats after treatment with 50 μg α2-GP (FIG. 3, curve 1) or after 60 min of restrained-stress (FIG. 3, curve 2). The resting insulin levels ranged from 8.5 to 11 μU/ml, so that the maximal Δ-insulinemia of −8.0 seen is quite dramatic. This effect suggests that α2-GP not only antagonizes the effects of circulating insulin but may also block the release of new insulin.

Example 5

Figure 4:
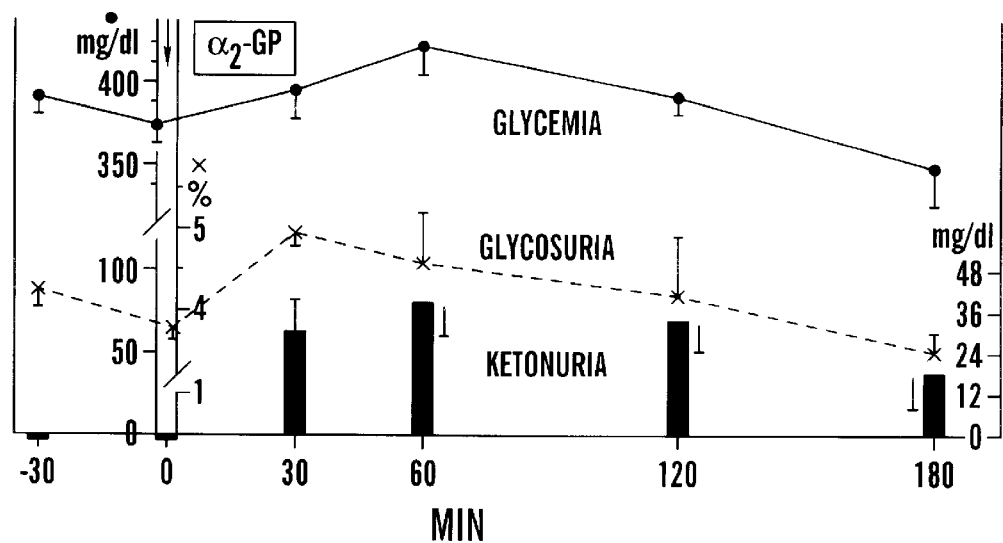
FIG. 4 shows the acute aggravation of moderate streptozotocin-induced diabetes by α2-GP. Glycemia (in mg/dl, left y-axis), glycosuria (in %, middle y-axis), and ketonuria (in mg/dl, right y-axis) are monitored before and after the injection of 200 μg α2-GP. Results are mean ± s.e.m., n=5.

Testing Pure α2-GP Capability to Cause Diabetogenic-Induced Derangement and Acute Aggravation Rats with moderate streptozotocin-induced diabetes were used as a model system. The 5% residual insulin corresponds to a 95% destruction of insulin cells to test if pure α2-GP could cause diabetogenic-induced derangement and acute aggravation, a signature of GH administration in humans. M. Press, et al., *New Engl. J. Med.* 310:810 (1984), which is hereby incorporated by reference. To obtain this, which will induce a moderate diabetes that permits the rat to live without receiving insulin, a dose of streptozotocin 45 mg/100 g is used instead of the standard 50 mg/100 g diabetogenic dose. Due to individual variations against the drug, only rats showing glycosuria without ketonuria are selected and controlled during 5 days before beginning the experiment. The 5% residual insulin prevents diabetic derangement. If insulin is neutralized by psychological stress, then ketonuria is induced as demonstrated in a pioneering work by L. C. Hinkle, et al., *J. Clin. Invest.,* 29:754 (1950), which is hereby incorporated by reference. Within 30 min of an injection of 200 μg α2-GP, significant increases in glycemia and glycosuria, and most notably, a dramatic induction of ketonuria were observed (FIG. 4). Consistent with the results of others, the treatment of these rats with rat-GH led to a similar induction of ketonuria, but after a lag time of 120 min. U. Keller, H. Schnell, J. Girard, and W. Stauffacher, *Diabetologia* 26:103 (1984), which is hereby incorporated by reference. The induction of ketonuria by both α2-GP and rat-GH were unchanged by adrenal medullectomy indicating that adrenal catecholamine hormones are not involved in this response. Adrenal medullectomy also had no effect on the α2-GP induced hyperglycemia, confirming that the actions of α2-GP do not require adrenal hormones. L. Vargas and M. E. Kawada, *Horm. Metab. Res.* 8:383 (1976), which is hereby incorporated by reference.

Example 6

Amino-terminal Sequence Analysis of α2-GP

Sequence analysis showed that the 8 amino-terminal residues of α2-GP were identical to human serum transferrin ("hsTf"). Approximately 5 μg of α2-GP were blotted onto PVDF and sequenced on an Applied Biosystems Model 470A protein sequencer with an online PTH analyzer. M. W. Hunkapiller, K. Grandlund-Moyer and N. W. Whiteley, in *Methods of Protein Microcharacterization,* J. E. Shively, Ed., Humana Press, Clifton, N.J., (1986) pp. 223–247, which is hereby incorporated by reference. This sequencer is part of the Analytical and Synthesis Facility at Cornell University, led by Dr. T. W. Thannhauser. Only 11 cycles of sequencing were analyzed at the amino terminal due to low signal to noise ratios. The sequence reported by this method is the following: C|V-C|P-D-K-T(A)-V(N)-R(L)-W-X-G-X (SEQ. ID. No. 1), where the vertical bars indicate that both possibilities are equally probable, the bracketed amino acid residues are less probable than the unbracketed ones, and X stands for any amino acid residue. A search of a database of sequences available through the GCG package version 7.3 was conducted, (Genetics Computer Group, Inc., University Research Park, Madison, Wis. 53711), using as input the different possible sequences that could be formed with the above result (for example, VPDKTVRWXGX (SEQ. ID. No. 2)). The program 'blast' (GCG Package) found that the first eight amino acid residues of this sequence are identical to the corresponding residues of human serum transferrin (SWISS PROT code P02787)), a well-studied protein involved in iron transport. To confirm this match, the properties of α2-GP were compared with commercially available hsTf (Sigma Chemical Co., St. Louis, Mo.).

Example 7

Figure 6B:
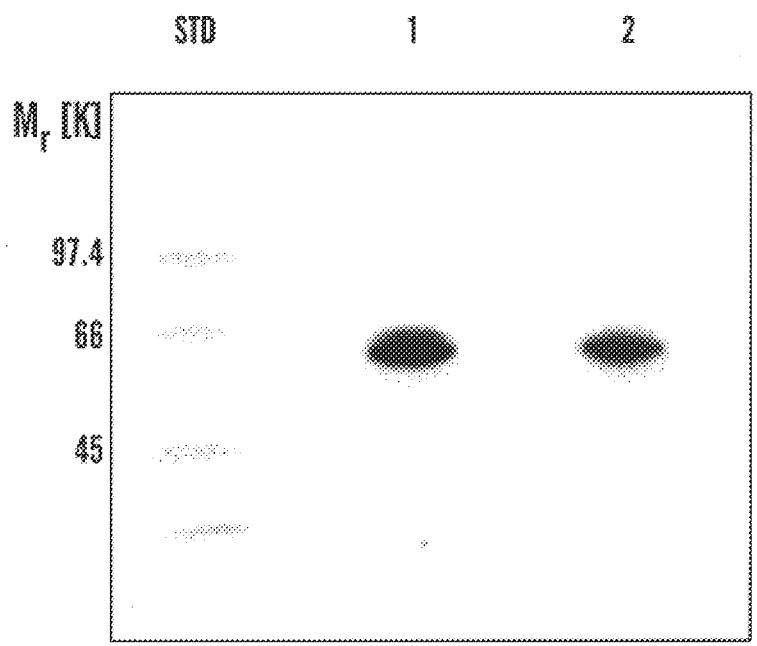
FIG. 6B shows a Western Blot analysis of hsTf (Sigma) (lane 1) and α2-GP (lane 2). A doublet is observed only for lane 1, showing that hsTf (Sigma) is less homogeneous than α2-GP (lane 2).

Identification of α2-GP as human serum transferrin

α2-GP ran identically with hsTf on SDS-gel electrophoresis (see FIG. 6A), and was recognized as well as hsTf by an anti-hsTf antibody (see FIG. 6B). The mouse monoclonal antibody against human serum transferrin, TW4.20, was used. Dr. M. Orlandini, Siena, Italy. M. Orlandini, A. Santucci, A. Tramontano, P. Neri and S. Oliviero, *Protein Sci.*, 3:1476, (1994), which is hereby incorporated by reference. Since TW4.20 recognizes hsTf under non-reducing conditions, both proteins were treated with 200 mM N-ethylmaleimide, and separated by SDS-PAGE. The observed difference in electrophoretic migration is due to the presence of N-ethylmaleimide. Proteins separated by SDS-PAGE were transferred to an Immobilon-P membrane (Millipore, Marlborough, Mass.) using a semi-dry electroblotter (ISS-Enprotech) as described in J. Kyhse-Andersen, *J. Biophys. Biochem. Methods*, 10:203 (1984), which is hereby incorporated by reference. Membranes were blocked for 1 hour at room temperature in TTBS (25 mM Tris-HCl pH 7.5, 150 mM NaCl, 0.1% Tween-20) containing 2.5% (w/v) BSA and then probed overnight at 4° C. with a mouse monoclonal antibody TW4.20 (1:1000) in TTBS containing 1% BSA. Blots were washed four times with TTBS, incubated for 1 hour at room temperature with peroxidase-coupled goat anti-mouse IgG (Gibco/BRL, Grand Island, N.Y.; 1:10,000) in TTBS containing 1% BSA, washed, and bands were detected by chemiluminescence.

Example 8

Figure 5:
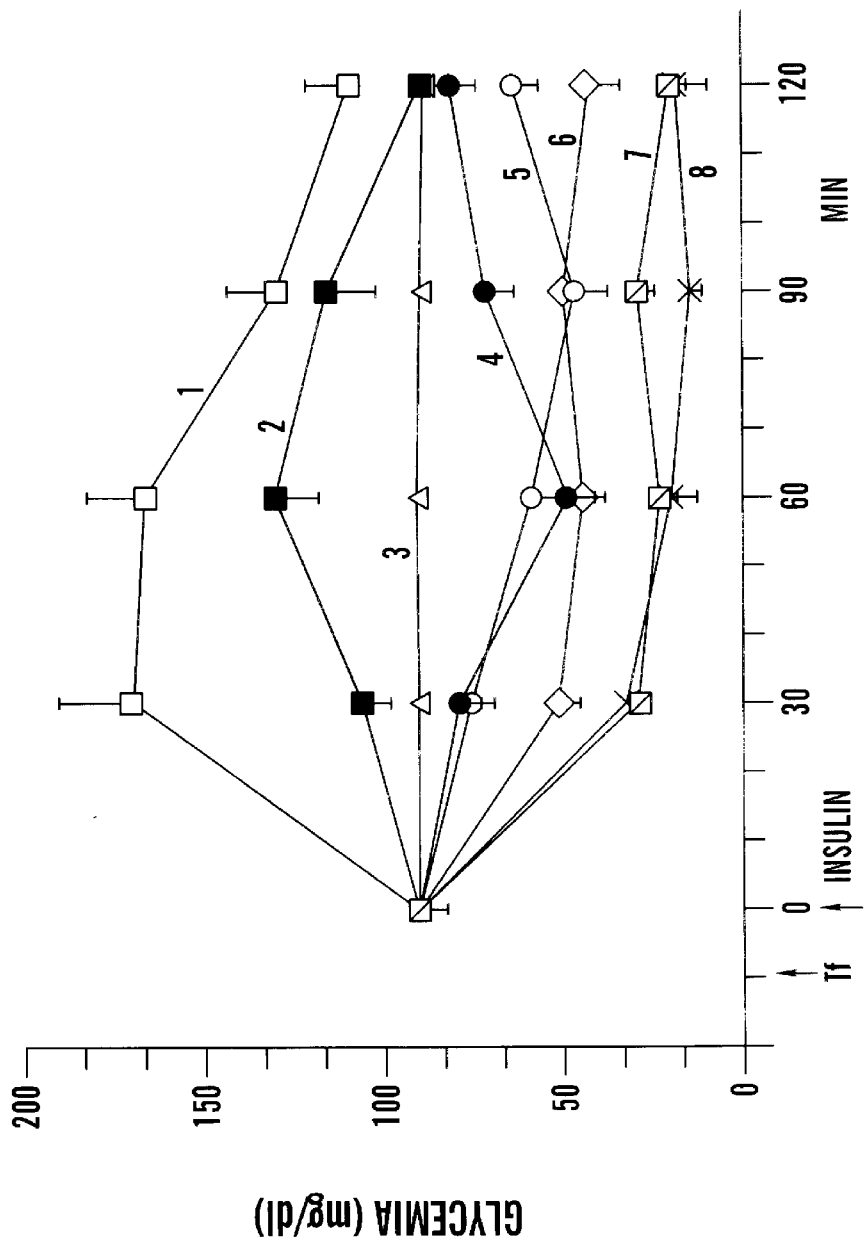
FIG. 5 shows the effect of 200 μg of apo-hsTf injected alone (curve 1), 200 μg of holo-human serum transferrin ("hsTf") (curve 2), 0.5 ml saline control (curve 3), 200 μg of holo-hsTf 10 min before insulin (curve 4), 200 μg of apo-hsTf 10 min before insulin (curve 5), 200 mg of fully non-glycosylated recombinant apo-hsTf 10 min. before insulin (curve 6), 200 μg of apo-ovoTf 10 min. before insulin (curve 7), and insulin control (curve 8) on serum glucose levels.

Ability of human serum transferrin to induce hyperglycemia and to antagonize insulin induced hypoglycemia In vivo studies showed that both apo-hsTf (iron free) and holo-hsTf (diferric) induced hyperglycemia and antagonized insulin-induced hypoglycemia similarly to α2-GP. The results are clearly depicted in FIG. 5: effect of 200 μg of apo-hsTf injected alone (curve 1), 200 μg of holo-hsTf (curve 2), 0.5 ml saline control (curve 3), 200 μg of holo-hsTf 10 min before insulin (curve 4), 200 μg of apo-hsTf 10 min before insulin (curve 5), 200 μg of fully non-glycosylated recombinant apo-hsTf 10 min. before insulin (curve 6), 200 μg of apo-ovoTf 10 min. before insulin (curve 7), and insulin control (curve 8). Apo and holo non-glycosylated recombinant hsTf behaved similarly and only the apo curve is shown for clarity. For the experiments where insulin was administered n=5, for induced-hyperglycemia produced by apo-hsTf n=3, and for induced-hyperglycemia produced by holo-hsTf n=2. Values for apo-hsTf (curve 1) are p<0.05 and values for both transferrins (curves 4 and 5) are all significant except for holo-hsTf at 60 min (curve 4) and apo-hsTf at 90 min (curve 5). Curve 5 is very similar to the α-GP curve (FIG. 2, curve 2). Insulin antagonism of ovoTf was measured on a separate group of rats and included tests with apo-ovoTf (n=4), or holo-ovoTf (n=3), given 10 min. before insulin, and an insulin control (n=3). The apo-ovoTf and the holo-ovoTf time-courses were indistinguishable from the insulin control. For unknown reasons, the rats for these studies had a basal glycemia of ca. 120 mg/dl so in order to include the apo-ovoTf data on this plot a value of 27 mg/dl was substracted from each point. Results are mean ± s.e.m.

In addition to this direct biochemical evidence for the identity of α2-GP and hsTf, further support is provided by the knowledge that hsTf is synthesized in the liver, and that the rat Tf gene is induced by GH. Idzerda, R. L., et al., *Mol. Cell. Biol.* 9:5154 (1989),which is hereby incorporated by reference. These lines of evidence strongly imply that α2-GP is hsTf, with the caveat that since α2-GP is defined by activity, it may only correspond to a subset of the circulating transferrin. Either form of transferrin can be used in this invention.

This novel role for hsTf in the regulation of glucose metabolism is completely unexpected, but may tie in with a number of previous observations. For instance, it suggests a physiological role for the observed insulin-induced increase in the number of cell surface Tf receptors (C. Akin and G. Sonnenfeld, *Cancer Lett.* 69:51 (1993), which is hereby incorporated by reference), and it may partly explain the activity of Tf as a growth factorfor muscle cells (G. Markelonis and T. H. Oh, *Proc. Natl. Acad. Sci.* 76:2470 (1979) and E. Ozawa, *Rev. Physiol. Biochem. Pharmacol.* 113:90 (1989), which are hereby incorporated by reference) and pituitary cells (D. A. Sirbasku, R. Pakala, H. Sato, and J. E. Eby, *Biochemistry* 30:7466 (1991), which is hereby incorporated by reference). Also, it may help explain the large body of literature suggesting a connection between iron and diabetes. J. B. Redmon, *Mayo Clin. Proc.* 69:90 (1994), which is hereby incorporated by reference. Although previous research could not demonstrate a convincing correlation between iron levels in the liver and type-II diabetes, the above results suggest that it may be hsTf, not iron, that plays a role in the pathophysiology of diabetes. Similarly, since hsTf is induced by estrogen (D. C. Lee, et al.,*J. Biol. Chem.* 253:3494 (1978), which is hereby incorporated by reference), is elevated acromegaly, and is decreased in hypopituitarism (M. Matsubara, et al., "Plasma Transferrin Levels in Abnormal Endocrine States—I. Changes in Hypophysial Diseases Before and After Treatment," *Horm. Metabol. Res.* 20:506–09 (1988), which is hereby incorporated by reference), it could play a role in the insulin resistance associated with stress (L. Vargas, et al., *Horm Metab. Res.* 6:275 (1974), which is hereby incorporated by reference), pregnancy and infection (J. C. Davis, et al., *Lancet* 2:1343 (1978), which is hereby incorporated by reference). Interestingly, non-enzymatically glycated hsTf is also found to be one of the markers of short-term blood glucose control (S. F. Kemp, et al., *J. Pediatrics* 105:394 (1984), which is hereby incorporated by reference).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of antagonizing transferrin inhibition of blood glucose metabolism regulated by insulin in a mammal comprising:

administering to the mammal an antibody which can bind to transferrin under conditions suitable to modulate blood glucose levels.

2. A method according to claim 1, wherein the antibody is a monoclonal antibody.

3. A method according to claim 1, wherein the mammal is a human.

4. A method according to claim 1, wherein said administering an antibody is carried out orally, intravenously, intramuscularly, intraperitoneally, subcutaneously, by intranasal instillation, by application to mucous membranes, or by instillation into hollow organ walls.

5. A method according to claim 1, wherein the transferrin is human transferrin.

6. A method according to claim 1, wherein the transferrin is selected from a group consisting of apo-transferrin, monoferric transferrin with an iron atom attached to the N-terminal domain binding site, monoferric transferrin with an iron atom attached to the C-terminal domain binding site, and diferric transferrin.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:1:

Cys Val Cys Pro Asp Lys Thr Ala Val Asn Arg Leu Trp Xaa Gly Xaa
   1            5                   10                   15

( 2 ) INFORMATION FOR SEQ ID NO:2:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:2:

Val Pro Asp Lys Thr Val Arg Trp Xaa Gly Xaa
   1            5                   10